(12) United States Patent
Sulger

(10) Patent No.: US 8,535,287 B2
(45) Date of Patent: Sep. 17, 2013

(54) MAGNETIZABLE TAMPON DEVICE

(76) Inventor: Christian Sulger, Erolzheim (DE)

(*) Notice: Subject to any disclaimer, the term of this patent is extended or adjusted under 35 U.S.C. 154(b) by 857 days.

(21) Appl. No.: 12/450,750

(22) PCT Filed: Jun. 23, 2007

(86) PCT No.: PCT/DE2007/001111
§ 371 (c)(1),
(2), (4) Date: Oct. 9, 2009

(87) PCT Pub. No.: WO2009/000220
PCT Pub. Date: Dec. 13, 2008

(65) Prior Publication Data
US 2010/0136088 A1    Jun. 3, 2010

(51) Int. Cl.
*A61F 13/20* (2006.01)

(52) U.S. Cl.
USPC ..................... 604/385.18; 604/904

(58) Field of Classification Search
USPC ................ 604/385.17–835.18, 904
See application file for complete search history.

(56) References Cited

U.S. PATENT DOCUMENTS

| | | | | |
|---|---|---|---|---|
| 4,405,323 A | * | 9/1983 | Auerbach | 604/285 |
| 5,079,006 A | * | 1/1992 | Urquhart | 424/422 |
| 7,176,344 B2 | * | 2/2007 | Gustafson et al. | 604/361 |
| 7,179,344 B1 | * | 2/2007 | Montano et al. | 156/247 |
| 2004/0064114 A1 | | 4/2004 | David et al. | |
| 2008/0033383 A1 | * | 2/2008 | Cantor et al. | 604/361 |
| 2010/0036350 A1 | * | 2/2010 | Heo | 604/385.01 |
| 2010/0056963 A1 | * | 3/2010 | Shaviv | 601/46 |

FOREIGN PATENT DOCUMENTS

| | | |
|---|---|---|
| DE | 34 10 715 | 10/1985 |
| DE | 20 2006 005 424 | 8/2006 |
| GB | 1 283 521 | 7/1972 |
| GB | 2 291 374 | 1/1996 |
| WO | WO 00/66062 | 11/2000 |

OTHER PUBLICATIONS

International Search Report.
U.S. Appl. No. 60/893,387, filed Mar. 7, 2007.

* cited by examiner

*Primary Examiner* — Lynne Anderson
(74) *Attorney, Agent, or Firm* — Collard & Roe, P.C.

(57) ABSTRACT

In a tampon device for introduction into the female vulva, comprising a packing material of absorbent material for the absorbance of menstrual fluid, menstrual pains such as painful myogeloses and cramps in the region of the vaginal musculature are alleviated or stopped in that the packing material incorporates a magnetic substance that interacts with the earth's magnetic field.

14 Claims, 2 Drawing Sheets

MAGNETIZABLE TAMPON DEVICE

CROSS REFERENCE TO RELATED APPLICATIONS

This application is the National Stage of PCT/DE2007/001111 filed on Jun. 23, 2007. The international application under PCT article 21 (2) was not published in English.

The invention relates to a tampon device for insertion into the female vulva, comprising a packing material of absorbent material for absorbance of menstrual fluid, which packing material incorporates a magnetic substance that interacts with the earth's magnetic field.

Tampon devices of the above type are used in the prior art for collection and short-term storage of menstrual fluid in the vulva in order not to restrict the freedom of movement of a person using the tampon device. However, the known devices suffer from the drawback that the simultaneous treatment of menstrual pains in a wider sense is not possible.

US 2004/0064114 A1 discloses a system for the detection of the moisture content of a moisture absorbing material, in which a sensor emits an electric output signal depending on the amount of aqueous liquid present in the material.

It is an object of the invention to provide a tampon device by means of which menstrual pains in a wider sense, such as myogeloses and cramps in the region of the vaginal musculature can be alleviated or stopped.

For a device of the above type this object is achieved according to a first aspect of the invention in that the magnetic substance is in the form of a bar magnet disposed for orientation along the longitudinal axis of the cylindrical body, which cylindrical body has a length ranging from approximately 2.0 cm to 5.0 cm and a diameter ranging from approximately 0.5 cm to 1.5 cm, the magnetic field caused by the magnetic substance having a strength equal to from 0.5 to 2 times the strength of the earth's magnetic field. The magnetic substance is such that it can be magnetized by a magnetization process known per se so as to permanently produce a magnetic field of the strength specified above.

According to a second aspect of the invention, the object is achieved for a device of the above type in that the packing material encloses a power source, a magnetic substance surrounded by an electric coil, and activating means for controlling the current flowing through the coil. The magnetic substance is such that its degree of magnetization can change due to the action of the alternating magnetic field produced by the coil, and a magnetic field is produced whose strength varies with time in a predefined manner.

Preferred embodiments of the invention are the subject matter of the subordinate claims pertaining to the respective independent claims.

In the tampon device of the invention, the feature according to the first aspect to the effect that the packing material incorporates a magnetic substance that interacts with the earth's magnetic field ensures that the constant movement of the person wearing the tampon device causes continual changes in the orientation of the magnetic field caused by the magnetic substance with reference to the earth's magnetic field, whilst the force of the resultant magnetic field in the case of co-orientation is equal to the sum of the two fields and in the case of contra-orientation to the difference between the stronger magnetic field and the weaker magnetic field.

In the remaining intermediate positions occurring during the period of wearing the tampon device of the invention, the force of the resultant magnetic field takes on an intermediate position between these extreme values. A continual change in orientation of the position of the tampon device of the invention as caused by movement thus results in continual change of random magnitude in the total magnetic field surrounding the magnetic substance. The alternating field thus caused is suitable for relieving menstrual cramps of the vaginal musculature and also myotonia and myogeloses.

In the tampon device of the invention according to the second aspect the combination of features to the effect that the packing material incorporates a power source, a magnetic substance surrounded by an electric coil, and activating means for controlling the electric current flowing through the coil has the result that a magnetic field varying with time as predefined by the activating means is produced and has a direct effect on the ambient muscle tissue and helps to alleviate or even completely stop the menstrual pains. The activating means can be controlled by means of a programmable chip, or they can include a hardwired analog circuit.

The solutions according to the invention both have the advantage over prior attempts to solve the problem in that absolutely no chemical or pharmaceutical substances are required.

According to preferred embodiments of the device of the invention according to the first aspect provision is made for the magnetic substance to be of iron, copper, or nickel.

The magnetic substance is preferably in the form of a bar magnet and is likewise preferably incorporated inside the packing material.

According to another preferred embodiment of the device of the invention according to the first aspect, provision is made for the packing material to be substantially in the form of a cylindrical body having rounded end faces, and the magnetic substance is provided in the region of the longitudinal axis of the cylindrical body. When the magnetic substance is in the form of a bar magnet, it is preferably oriented along the longitudinal axis of the cylindrical body.

The cylindrical body of the device of the invention preferably has a length ranging from approximately 2.0 cm to 5.0 cm and a diameter ranging from approximately 0.5 cm to 1.5 cm.

When the magnetic substance is in the form of a bar magnet, it preferably has a length ranging from 0.5 mm to 10 mm and a diameter ranging from 0.5 mm to 5 mm.

According to an important preferred embodiment of the device of the invention according to the first aspect, provision is made for a magnetic field caused by means of the magnetic substance to have a strength which is equal to from 0.5 times to 2 times the strength of the earth's magnetic field.

According to preferred embodiments of the device of the invention according to the second aspect, provision is made for the activating means to produce a square wave voltage or a sinusoidal voltage curve.

Here again, the magnetic substance is preferably of iron, copper, or nickel and likewise preferably in the form of a bar magnet located inside the coil.

According to another preferred embodiment of the device of the invention according to the second aspect, provision is made for the power source, the electric coil surrounding the magnetic substance, and the activating means to be located inside the packing material.

According to another preferred embodiment of the device of the invention according to the second aspect, provision is made for the packing material to be substantially in the form of a cylindrical body having rounded end faces, the power source, the electric coil surrounding the magnetic substance, and the activating means being provided in the region of the longitudinal axis of the cylindrical body.

In addition, in the device of the invention according to the second aspect, the magnetic substance is in the form of a bar magnet which can be disposed for orientation in the direction of the longitudinal axis of the cylindrical body. The cylindrical body preferably has a length ranging from approximately 2.0 cm to 5.0 cm and a diameter ranging from approximately 0.5 cm to 1.5 cm.

The device of the invention is explained below with reference to preferred embodiments illustrated in the figures of the drawing, in which.

Figure 1:
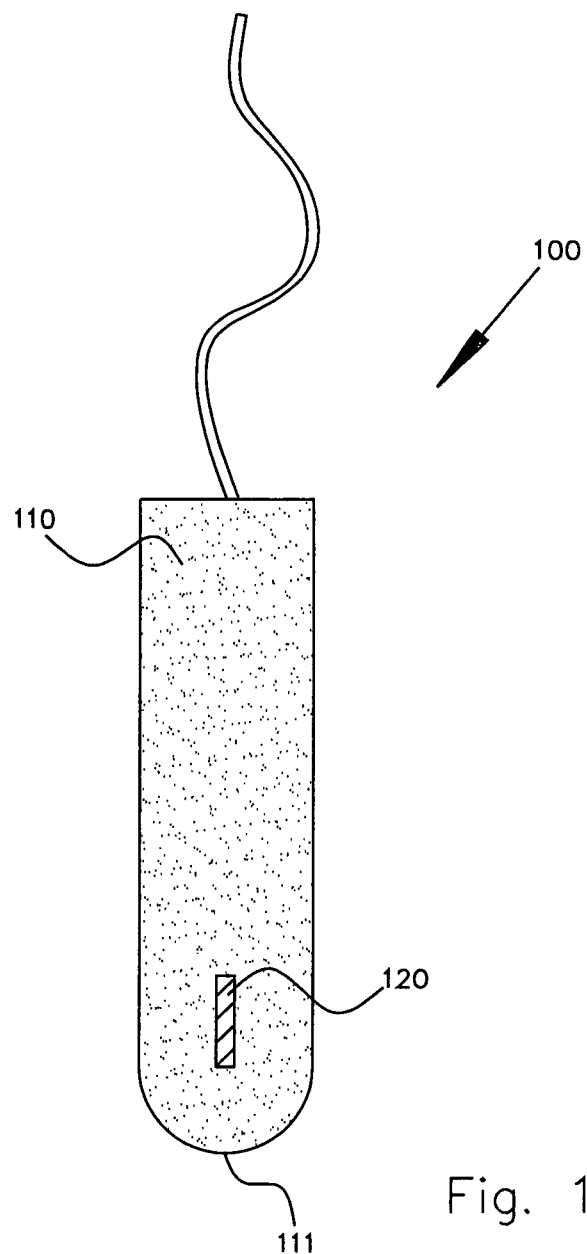
FIG. 1 shows a first preferred embodiment of the device of the invention in a diagrammatic cross-sectional view.

The tampon device 100 of the invention illustrated in FIG. 1 for insertion into the female vulva contains a packing material 110 of absorbent material for absorbance of menstrual fluid, and a magnetic substance 120 is incorporated in the packing material 110, which magnetic substance interacts with the earth's magnetic field. The magnetic substance 120 is of iron and in the form of a bar magnet disposed inside the packing material 110.

The packing material 110 is substantially in the form of a cylindrical body with rounded end faces 111, and the bar magnet is disposed in the region of the longitudinal axis of the cylindrical body and is oriented in the direction of the longitudinal axis of the cylindrical body.

The cylindrical body has a length ranging from approximately 3.0 cm and a diameter of approximately 0.7 cm. The bar magnet has a length of approximately 3 mm and a diameter of approximately 2 mm.

The magnetic field produced by the bar magnet has a strength equal to approximately 2 times the strength of the earth's magnetic field.

Figure 2:
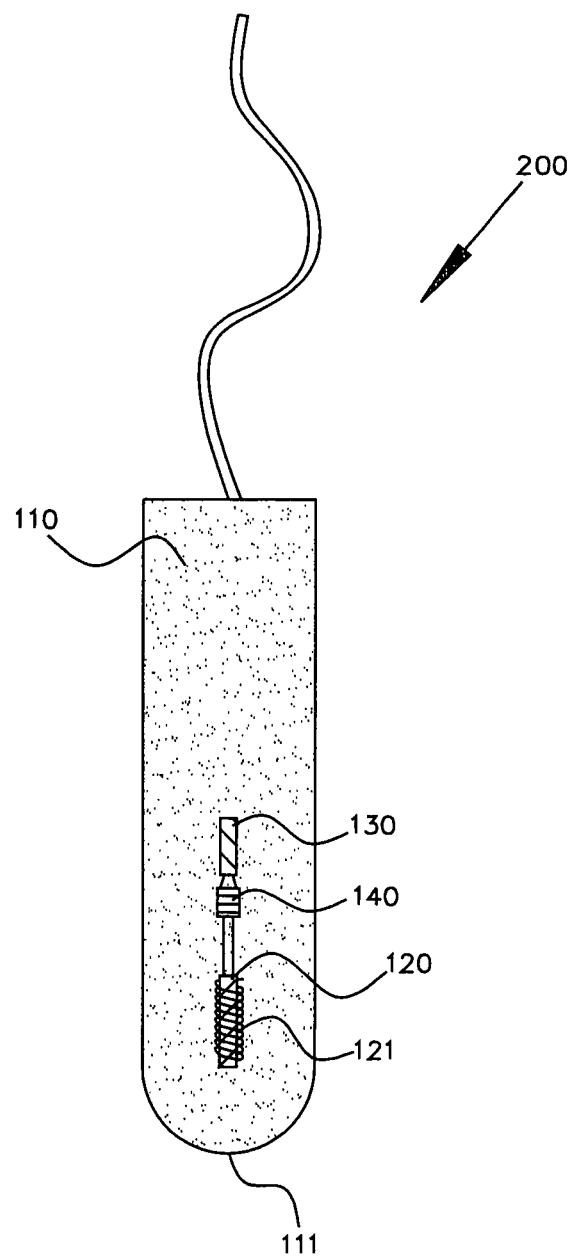
FIG. 2 shows a second preferred embodiment of the device of the invention in a diagrammatic cross-sectional view.

The tampon device 200 of the invention illustrated in FIG. 2 for introduction into the female vulva is in principle similar to the tampon device 100 illustrated in FIG. 1 and contains a packing material 110 of absorbent material for the absorbance of menstrual fluid, and the packing material 110 incorporates a power source 130, a magnetic substance 120 surrounded by an electric coil 121, and activating means 140 for controlling the electric current flowing through the coil 121. The activating means 140 produce a square wave voltage, which produces a corresponding alternating magnetic field in the coil 121.

Here again, the packing material 110 is substantially in the form of a cylindrical body with rounded end faces 111, and the power source 130, the magnetic substance 120 surrounding the electric coil 121, and the activating means 140 are provided in the region of the longitudinal axis of the cylindrical body.

The exemplary embodiments of the invention explained above merely serve the purpose of providing a better understanding of the teaching of the invention as defined in the claims, which teaching is as such not restricted to said exemplary embodiments.

The invention claimed is:

1. A tampon device for introduction into the female vulva, comprising a packing material of absorbent material for the absorbance of menstrual fluid, wherein said packing material is substantially in the form of a cylindrical body with rounded end faces and incorporates a magnetic substance which interacts with the earth's magnetic field and is disposed in the region of a longitudinal axis of the cylindrical body, wherein said magnetic substance is in the form of a bar magnet having a length ranging from 0.5 mm to 10 mm and a diameter ranging from 0.5 mm to 5 mm which is disposed for orientation in the direction of the longitudinal axis of the cylindrical body, said cylindrical body having a length ranging from approximately 2.0 cm to 5.0 cm and a diameter ranging from approximately 0.5 cm to 1.5 cm.

2. The device according to claim 1, wherein the magnetic substance is composed of iron.

3. The device according to claim 1, wherein the magnetic substance is composed of copper.

4. The device according to claim 1, wherein the magnetic substance is composed of nickel.

5. The device according to claim 1, wherein said magnetic substance is disposed inside the packing material.

6. The device according to claim 1, wherein the diameter of the bar segment ranges from 2 mm to 5 mm.

7. A tampon device for introduction into the female vulva, comprising a packing material of absorbent material for the absorbance of menstrual fluid, wherein said packing material incorporates a power source, a magnetic substance surrounded by an electric coil, and activating means for controlling the electric current flowing through said coil, wherein said magnetic substance is in the form of a bar magnet disposed inside said coil, wherein said packing material is substantially in the form of a cylindrical body with rounded end faces, and wherein said power source, said magnetic substance surrounded by said electric coil, and said activating means are disposed in a region of a longitudinal axis of said cylindrical body.

8. The device according to claim 7, wherein said activating means produce a square wave voltage.

9. The device according to claim 7, wherein said activating means produce a sinusoidal voltage curve.

10. The device according to claim 7, wherein the magnetic substance is composed of iron.

11. The device according to claim 7, wherein the magnetic substance is composed of copper.

12. The device according to claim 7, wherein the magnetic substance is composed of nickel.

13. The device according to claim 7, wherein said magnetic substance is in the form of a bar magnet disposed for orientation in the direction of the longitudinal axis of said cylindrical body.

14. The device according to claim 7, wherein said cylindrical body has a length ranging from approximately 2.0 cm to 5.0 cm and a diameter ranging from approximately 0.5 cm to 1.5 cm.

\* \* \* \* \*